United States Patent

Pasquier et al.

(10) Patent No.: US 6,773,463 B2
(45) Date of Patent: Aug. 10, 2004

(54) AGENT AND METHOD FOR DYEING KERATIN FIBERS

(75) Inventors: Cécile Pasquier, Marly (CH); Véronique Charrière, Courtaman (CH); Hans-Jürgen Braun, Überstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 247 days.

(21) Appl. No.: 10/110,116

(22) PCT Filed: Jun. 29, 2001

(86) PCT No.: PCT/EP01/07494
§ 371 (c)(1),
(2), (4) Date: Apr. 5, 2002

(87) PCT Pub. No.: WO02/22093
PCT Pub. Date: Mar. 21, 2002

(65) Prior Publication Data
US 2003/0070239 A1 Apr. 17, 2003

(30) Foreign Application Priority Data
Sep. 15, 2000 (DE) .......................... 100 45 600

(51) Int. Cl.⁷ .................................. A61K 7/13
(52) U.S. Cl. ................ 8/405; 8/426; 8/437; 8/451; 8/454; 8/461; 8/462; 8/463; 548/181
(58) Field of Search .................. 8/405, 426, 437, 8/451, 454, 461, 462, 463; 548/181

(56) References Cited

U.S. PATENT DOCUMENTS

| | | | |
|---|---|---|---|
| 3,577,427 A | 5/1971 | Pilgram | 260/304 |
| 4,620,850 A | 11/1986 | Bachmann | 8/406 |
| 5,055,110 A | 10/1991 | Lim et al. | 8/405 |

FOREIGN PATENT DOCUMENTS

| WO | 01 103 79 A | 2/2001 |
|---|---|---|
| WO | 01 47485 A | 7/2001 |

OTHER PUBLICATIONS

Journal Fuer Praktische Chemie 327 (3), pp. 487–504, 1985.*
Journal of Organic Chemistry 36 91), 1971 pp. 207–209.
Recueil Trav. Chim. Pay–Bas. 86 (12), pp. 1159–1181, 1967.
Journal of Medicinal Chemistry, vol. 17(2), pp. 203–206, 1974.
Journal of the Chemical Society (B), 1967, pp. 909–911.

\* cited by examiner

*Primary Examiner*—Yogendra N. Gupta
*Assistant Examiner*—Eisa Elhilo
(74) *Attorney, Agent, or Firm*—Michael J. Striker

(57) ABSTRACT

The present invention relates to a fiber-dyeing agent (A) prepared by mixing two components (A1) and (A2), said agent being characterized in that component (A1) contains at least one compound of formula (I)

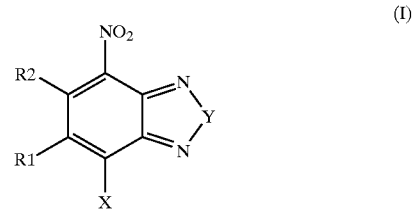

wherein X denotes a halogen atom, a methoxy group or an ethoxy group; Y denotes an oxygen atom, a sulfur atom or a selenium atom; R1 and R2 are equal or different and independently of each other denote hydrogen, a halogen atom, a ($C_1$–$C_4$)-alkyl group, a halogen-substituted ($C_1$–$C_4$)-alkyl group, a ($C_1$–$C_4$)-alkoxy group, a nitro group, an acetamido group or an $NR^aR^b$ group, wherein the $R^a$ and $R^b$ groups are equal or different and independently of each other denote hydrogen, a ($C_1$–$C_4$)-alkyl group, an optionally substituted aromatic carbon ring or a ($C_1$–$C_4$)-alkanecarbonyl group, or $R^a$ and $R^b$ together with the nitrogen atom form a heterocyclic ($C_3$–$C_6$) group, and component (A2) contains at least one compound from the group consisting of amines, aminonitrobenzenes and phenols; to a method for dyeing hair by use of said agent, and to a multicomponent kit.

13 Claims, No Drawings

AGENT AND METHOD FOR DYEING KERATIN FIBERS

The object of the present invention is an agent for dyeing keratin fibers, for example silk, wool or hair, particularly human hair, and which contains a combination of (i) at least one 4-nitro-2,1,3-benzoxadiazole derivative, 4-nitro-2,1,3-benzothiadiazole derivative or 4-nitro-2,1,3-benzoselenadiazole derivative and (ii) at least one amine, aminonitrobenzene or phenol, and a method for dyeing keratin fibers by use of said dyeing agent.

Depending on the starting color of the hair to be dyed and the desired final result, hair colorants are divided mainly into oxidative colorants and toners. Oxidative hair colorants are very well suited for covering higher proportions of gray hair. The oxidative colorants used for a gray proportion of up to 50% are usually referred to as oxidative toners whereas the oxidative colorants used for hair with a proportion of gray hair greater than 50%, or for "brightening", are usually referred to as oxidative colorants. Direct dyes are contained mainly in non-oxidative colorants (toners). Because of their small molecular size, some direct dyes, for example the nitro dyes, can penetrate into hair and—at least in the outer regions—dye it directly. Such toners are very gentle to the hair and as a rule can withstand six to eight hair washings. Direct dyes, particularly nitro dyes, are also frequently used in oxidative colorants to create certain shades or to intensify the color.

Nevertheless, there still exists a great need for colorants capable of both intense and gentle coloration under mild conditions.

Surprisingly, we have now found that by use of a combination of (i) at least one-4-nitro-2,1,3-benzoxadiazole derivative, 4-nitro-2,1,3-benzothiadiazole derivative or 4-nitro-2,1,3-benzoselenadiazole derivative and (ii) at least one amine, aminonitrobenzene or phenol, intense colorations with a great variety of shades can be achieved under mild conditions gentle to the hair.

Hence, the object of the present invention is an agent for dyeing fibers (A), for example wool, silk, cotton or hair and particularly human hair, which is prepared by mixing two components (A1) and (A2) and is characterized in that component (A1) contains at least one compound of formula (I)

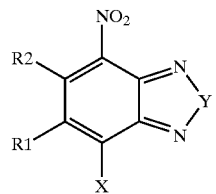

(I)

wherein X denotes a halogen atom (F, Cl, Br, I), a methoxy group or an ethoxy group; Y denotes an oxygen atom, a sulfur atom or a selenium atom; R1 and R2 are equal or different and independently of each other denote hydrogen, a halogen atom (F, Cl, Br, I), a ($C_1$–$C_4$)-alkyl group, a ($C_1$–$C_4$)-alkyl group substituted with a halogen atom (F, Cl, Br, I), a ($C_1$–$C_4$)-alkoxy group, a nitro group, an acetamido group or an $NR^aR^b$ group, wherein the $R^a$ and $R^b$ groups are equal or different and independently of each other denote hydrogen, a ($C_1$–$C_4$)-alkyl group, an optionally substituted aromatic carbon ring or a ($C_1$–$C_4$)-alkanecarbonyl group, or $R^a$ and $R^b$ together with the nitrogen atom form a heterocyclic ($C_3$–$C_6$) group (for example an imidazolidino, piperidino, pyrrolidino, pyrazolidino, piperazino or morpholino group); and component (A2) contains at least one compound selected from the group consisting of amines, aminonitrobenzenes and phenols.

Suitable compounds of formula (I) are, in particular, the following 4-nitro-2,1,3-benzoxadiazoles, 4-nitro-2,1,3-benzothiadiazoles and 4-nitro-2,1,3-benzoselenadiazoles:

4-chloro-7-nitro-2,1,3-benzoxadiazole; 4-bromo-7-nitro-2,1,3-benzoxadiazole; 4-fluoro-7-nitro-2,1,3-benzoxadiazole; 4-methoxy-7-nitro-2,1,3-benzoxediazole; 4-ethoxy-7-nitro-2,1,3-benzoxadiazole; 4-chloro-5,7-dinitro-2,1,3-benzoxadiazole; 5,7-dichloro-4-nitro-2,1,3-benzoxadiazole; 5,7-dibromo-4-nitro-2,1,3-benzoxadiazole; 7-chloro-4-nitro-5-diethylamino-2,1,3-benzoxadiazole; 5-amino-7-chloro-4-nitro-2,1,3-benzoxadiazole; 7-chloro-4-nitro-5-(1-piperidinyl)-2,1,3-benzoxadiazole; 4-chloro-7-nitro-2,1,3-benzothiadiazole; 4-bromo-7-nitro-2,1,3-benzothiadiazole; 4-methoxy-7-nitro-2,1,3-benzothiadiazole; 4-ethoxy-7-nitro-2,1,3-benzothiadiazole; 4-chloro-5,7-dinitro-2,1,3-benzothiadiazole; 4-bromo-5,7-dinitro-2,1,3-benzothiadiazole; 4,5-dichloro-7-nitro-2,1,3-benzothiadiazole; 5,7-dichloro-4-nitro-2,1,3-benzothiadiazole; 4,5-dibromo-7-nitro-2,1,3-benzothiadiazole; 5,7-dibromo-4-nitro-2,1,3-benzothiadiazole; 4,6-dichloro-5,7-dinitro-2,1,3-benzothiadiazole;4,6-dibromo-5,7-dinitro-2,1,3-benzothiadiazole; 5-chloro-7-fluoro-4-nitro-2,1,3-benzothiadiazole; 5-anilino-7-bromo-4-nitro-2,1,3-benzothiadiazole; 5-amino-7-chloro-4-nitro-2,1,3-benzothiadiazole; 7-bromo-5-(diethylamino)-4-nitro-2,1,3-benzothiadiazole; 4-chloro-5-methyl-7-nitro-2,1,3-benzothiadiazole;4-bromo-5-methyl-4-nitro-2,1,3-benzothiadiazole;7-bromo-5-(bromomethyl)-7-nitro-2,1,3-benzothiadiazole; N-(7-chloro-4-nitro-2,1,3-benzothiadiazole-5-yl)acetamide; 4-chloro-7-nitro-2,1,3-benzoselenadiazole; 4-bromo-7-nitro-2,1,3-benzoselenadiazole; 4-methoxy-7-nitro-2,1,3-benzoselenadiazole; 4-ethoxy-7-nitro-2,1,3-benzoselenadiazole; 5,7-dibromo-4-nitro-2,1,3-benzoselenadiazole; 5,7-dichloro-4-nitro-2,1,3-benzoselenadiazole; 7-bromo-5-methyl-4-nitro-2,1,3-benzoselenadiazole and 7-bromo-5-(bromomethyl)-4-nitro-2,1,3-benzoselenadiazole, among which the following compounds are particularly preferred: 4-chloro-7-nitro-2,1,3-benzoxadiazole; 4-bromo-7-nitro-2,1,3-benzoxadiazole; 4-chloro-7-nitro-2,1,3-benzothiadiazole; 4-bromo-7-nitro-2,1,3-benzothiadiazole; 4-chloro-7-nitro-2,1,3-benzoselenadiazole and 4-bromo-7-nitro-2,1,3-benzoselenadiazole.

Some of the compounds of formula (I) are commercially available. The compounds of formula (I), however, can also be prepared by methods of synthesis known from the literature, for example as described in the Journal of Organic Chemistry 36 (1), pages 207–209 (1971); Recueil Trav. Chim. Pays-Bas 86 (12), pages 1159–1181 (1967); Journal of Medicinal Chemistry, vol 17 (2), pages 203–206 (1974); Journal of the Chemical Society (B), 1967, pages 909–911 or in U.S. Pat. No. 3,577,427.

Suitable amines are aliphatic or aromatic (isocyclic or heterocyclic) compounds with at least one amino group. Suitable aminonitrobenzenes are aromatic (isocyclic or heterocyclic) compounds with at least one nitro group and at least one amino group, and suitable phenols are aromatic (isocyclic or heterocyclic) compounds with at least one hydroxyl group. Examples of the amines, aminonitrobenzenes and phenols contained in component (A2) are, in particular, the following:

ethanolamine; propylamine; 3-amino-1-propanol; butylamine; 4-amino-1-butanol; 1,4-diaminobenzene (p-phenylenediamine); 1,4-diamino-2-methylbenzene (p-toluylenediamine); 1,4-diamino-2,6-dimethylbenzene; 1,4-diamino-3,5-diethylbenzene; 1,4-diamino-2,5-dimethylbenzene; 1,4-diamino-2,3-dimethylbenzene; 2-chloro-1,4-diaminobenzene; 2,5-diaminobiphenyl; 1,4-diamino-2-hydroxymethylbenzene; 1,4-diamino-2-(2-hydroxyethoxy)benzene; 2-[2-(acetylamino)ethoxy]-1,4-diaminobenzene; N-methylaniline; 4-phenylaminoaniline; 4-dimethylaminoaniline; 4-diethylaminoaniline; 4-dipropylaminoaniline; 4-[ethyl(2-hydroxyethyl)amino]aniline; 4-[di(2'-hydroxyethyl)amino]aniline; 4-[di(2-hydroxyethyl)amino]-2-methylaniline; 4-[(2'-methoxyethyl)amino]aniline; 4-[(3'-hydroxypropyl)amino]aniline; 4-[(2,3-dihydroxypropyl)amino]aniline; 1,4-diamino-2-(2'-hydroxyethyl)benzene; 1,4-diamino-2-(1'-hydroxyethyl)benzene; 1,4-diamino-2-(1'-methylethyl)benzene; 1,4-diamino-2-(methoxymethyl)benzene; 1,4-diamino-2-(aminomethyl)benzene; 1,3-bis-[(4'-aminophenyl)(2'-hydroxyethyl)amino]-2-propanol; 1,4-bis-[(4-aminophenyl)amino]butane; 1,8-bis-(2',5'-diaminophenoxy)-3,6-dioxaoctane; phenol; hydroquinone; 2-methylphenol; 3-methylphenol; 4-methylphenol; 5-methyl-2-(1'-methylethyl)phenol; 4-aminophenol; 4-amino-3-methylphenol; 4-amino-3-(hydroxymethyl)phenol; 4-amino-3-fluorophenol; 4-methylaminophenol; 4-amino-2-(aminomethyl)phenol; 4-amino-2-(hydroxymethyl)phenol; 4-amino-2-fluorophenol; 4-amino-[(2'-hydroxyethyl)amino]-methylphenol; 4-amino-2-methylphenol; 4-amino-2-(methoxymethyl)phenol; 4-amino-2-(2'-hydroxyethyl)phenol; 5-aminosalicylic acid; 2,5-diaminopyridine; 2,4,5,6-tetraaminopyrimidine; 2,5,6-triamino-4-(1H)-pyrimidone; 4,5-diamino-1-(4'-methyl-benzyl)-1H-pyrazole; 4,5-diamino-1H-pyrazole; 4,5-diamino-1-(4'-methoxybenzyl)-1H-pyrazole; 4,5-diamino-1-(3'-methoxybenzyl)-1H-pyrazole; 4,5-diamino-1-(4'-chlorobenzyl)-1H-pyrazole; 4,5-diamino-1-(4'-methylphenyl)-1H-pyrazole; 4,5-diamino-1-(4'-methoxyphenyl)-1H-pyrazole; 4,5-diamino-1-(3'-methoxyphenyl)-1H-pyrazole; 4,5-diamino-1-(4'-chlorophenyl)-1H-pyrazole; 4,5-diamino-1-(2'-hydroxyethyl)-1H-pyrazole; 4,5-diamino-1-methyl-1H-pyrazole; 4,5-diamino-1-ethyl-1H-pyrazole; 4-amino-1-[(4'-methoxyphenyl)methyl]-5-(methylamino)-1H-pyrazole; 4-amino-5-[(2'-hydroxyethyl)amino]-1-(phenylmethyl)-1H-pyrazole; 4,5-diamino-1-methyl-3-phenyl-1H-pyrazole; 4,5-diamino-1-(2'-hydroxyethyl)-3-phenyl-1H-pyrazole; 4,5-diamino-1,3-dimethyl-1H-pyrazole; 4,5-diamino-3-methyl-1-phenyl-1H-pyrazole; 4,5-diamino-1-(1-isopropyl)-1H-pyrazole; 2-aminophenol; 2-amino-6-methylphenol; 2-amino-5-methylphenol; 1,4-diamino-2-(thiophen-2-yl)benzene; 1,4-diamino-2-(thiophen-3-yl)benzene; 1,4-diamino-2-(pyridin-3-yl)benzene; 1,2,4-trihydroxybenzene; N-(3-dimethylaminophenyl)urea; 2,6-diaminopyridine; 2-amino-4-[(2'-hydroxyethyl)-amino]anisole; 2,4-diamino-1-fluoro-5-methylbenzene; 2,4-diamino-1-methoxy-5-methylbenzene; 2,4-diamino-1-ethoxy-5-methylbenzene; 2,4-diamino-1-(2'-hydroxyethoxy)-5-methylbenzene; 2,4-di-[(2'-hydroxyethyl)amino]-1,5-dimethoxybenzene; 2,3-diamino-6-methoxypyridine; 3-amino-6-methoxy-2-(methylamino)pyridine; 2,6-diamino-3,5-dimethoxypyridine; 3,5-diamino-2,6-dimethoxypyridine; 1,3-diaminobenzene (m-phenylenediamine); 2,4-diamino-1-(2'-hydroxyethoxy)benzene; 2,4-diamino-1,5-di (2'-hydroxyethoxy)benzene; 1,3-diamino-4-(2,3-dihydroxypropoxy)benzene; 1,3-diamino-4-(3-hydroxypropoxy)benzene; 1,3-diamino-4-(2-methoxyethoxy)benzene; 1-(2'-aminoethoxy)-2,4-diaminobenzene; 2-amino-1-(2'-hydroxyethoxy)-4-methylaminobenzene; 2,4-diaminophenoxyacetic acid; 3-[di(2'-hydroxyethyl)amino]aniline; 4-amino-2-di[(2'-hydroxyethyl)amino]-1-ethoxybenzene; 5-methyl-2-(1-methylethyl)phenol; 3-[(2'-hydroxyethyl)amino]aniline; 3-[(2'-aminoethyl)amino]aniline; 1,3-2',4'-diaminophenoxy)propane; di(2',4'-diaminophenoxy)methane; 1,3-diamino-2,4-dimethoxybenzene; 2,6-bis-(2'-hydroxyethyl)aminotoluene; 4-hydroxyindole; 3-dimethylaminophenol; 3-diethylaminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methylphenol; 3-amino-2-chloro-6-methylphenol; 3-aminophenol; N-[(3'-hydroxyphenyl)amino]acetamide; 5-[(2-hydroxyethyl)amino-2-methylphenol; 5-[(2-hydroxyethyl)amino]-4-methoxy-2-methylphenol; 3-[(2'-hydroxyethyl)amino]phenol; 3-[(2'-methoxyethyl)-amino]phenol; 5-amino-2-ethylphenol; 5-amino-2-methoxyphenol; 2-(4'-amino-2'-hydroxyphenoxy)ethanol; 5-[(3'-hydroxypropyl)amino]-2-methylphenol; 3-[(2',3'-dihydroxy)propylamino]-2-methylphenol; 3-[(2'-hydroxyethyl)amino]-2-methylphenol; 2-amino-3-hydroxypyridine; 2,6-dihydroxy-3,4-dimethylpyridine; 5-amino-4-chloro-2-methylphenol; 1-naphthol; 1,5-dihydroxynaphthalene; 1,7-dihydroxynaphthalene; 2,3-dihydroxynaphthalene; 2,7-dihydroxynaphthalene; 2-methyl-1-naphthol acetate; 1,3-dihydroxybenzene (resorcinol); 1-chloro-2,4-dihydroxybenzene; 2-chloro-1,3-dihydroxybenzene; 1,2-dichloro-3,5-dihydroxy-4-methylbenzene; 1,5-dichloro-2,4-dihydroxybenzene; 1,3-dihydroxy-2-methylbenzene; 3,4-methylenedioxyphenol; 3,4-methylenedioxyaniline; 5-[(2'-hydroxyethyl)amino]-1,3-benzodioxole; 6-bromo-1-hydroxy-3,4-methylenedioxybenzene; 3,4-diaminobenzoic acid; 3,4-dihydro-6-hydroxy-1,4(2H)-benzoxazine; 6-amino-3,4-dihydro-1,4(2H)-benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolindione; 1,4-bis-[2'-hydroxyethyl)amino]-2-nitrobenzene; 1-(2'-hydroxyethyl)-amino-2-nitro-4-[di(2'-hydroxyethyl)amino]benzene; 1-amino-3-methyl-4-[(2'-hydroxyethyl)amino]-6-nitrobenzene; 4-[ethyl-(2'-hydroxyethyl)amino]-1-[(2'-hydroxyethyl)amino]-2-nitrobenzene hydrochloride; 4-[di(2'-hydroxyethyl)amino]-1-[(2'-methoxyethyl)amino]-2-nitrobenzene; 1-[(2',3'-dihydroxypropyl)amino]-4-methyl-(2'-hydroxyethyl)amino]-2-nitrobenzene; 1-[(2',3'-dihydroxypropyl)amino]-4-ethyl-(2'-hydroxyethyl)amino]-2-nitrobenzene hydrochloride; 1-(3'-hydroxypropylamino)-4-[(di-(2'-hydroxyethyl)amino]-2-nitrobenzene; 1-methylamino-4-[methyl-(2',3'-dihydroxypropyl)amino]-2-nitrobenzene; 2-[(4-amino-2-nitrophenyl)-amino]-5-dimethylaminobenzoic acid; 1-(2'-aminoethylamino)-4-[(di(2'-hydroxyethyl)-amino]-2-nitrobenzene; 1-amino-4-[(2'-hydroxyethyl)amino]-2-nitrobenzene; 2-amino-4,6-dinitrophenol; 1,4-diamino-2- nitrobenzene; 4-amino-2-nitrodiphenylamine; 1-amino-4-[(di(2'-hydroxyethyl)amino]-2-nitrobenzene hydrochloride; 1-amino-5-chloro-4-[(2'-hydroxyethyl)amino]-2-nitrobenzene; 4-amino-1-[(2'-hydroxyethyl)amino]-2-nitrobenzene; 4-[(2'-hydroxyethyl)methylamino]-1-(methylamino)-2-nitrobenzene; 1-amino-4-[(2',3'-dihydroxypropyl)amino]-5-methyl-2-nitrobenzene; 1-amino-4-(methylamino)-2-nitrobenzene; 4-amino-2-nitro-1-[(prop-2-en-1-yl)amino]benzene; 4-amino-3-nitrophenol; 4-[(2'-hydroxyethyl)amino]-3-nitrophenol;4-[(2-nitrophenyl)amino]phenol; 1-[(2'-aminoethyl)amino]-4-(2'-hydroxyethoxy)-2-nitrobenzene; 4-(2',3'-di-hydroxypropoxy)-1-[(2'-hydroxyethyl)amino]-2-nitrobenzene; 1-amino-5-chloro-4-[(2',3'-dihydroxypropyl)amino]-2-nitrobenzene; 5-chloro-1,4-[di-(2',3'-dihydroxypropyl)amino]-2-nitrobenzene; 2-[(2'-hydroxyethyl)amino]-4,6-dinitrophenol; 4-ethylamino-3-nitrobenzoic acid; 2-[(4'-amino-2'-nitrophenyl)amino]benzoic acid; 2-chloro-6-ethylamino-4-nitrophenol; 2-amino-6-chloro-4-nitrophenol; 4-[(3'-hydroxypropyl)-amino]-3-nitrophenol; 2,5-diamino-6-nitropyridine; 6-amino-3-[(2'-hydroxyethyl)amino]-2-nitropyridine; 3-amino-6-[(2'-hydroxyethyl)amino]-2-nitropyridine; 3-amino-6-(ethylamino)-2-nitropyridine;3-[(2'-hydroxyethyl)amino]-6-(methylamino)-2-nitropyridine; 3-amino-6-(methylamino)-2-nitropyridine; 6-(ethylamino)-3-[(2'-hydroxyethyl)amino]-2-nitropyridine; 1,2,3,4-tetrahydro-6-nitro-quinoxaline; 7-amino-3,4-dihydro-6-nitro-2H-1,4-benzoxazine; 1,2-diamino-4-nitrobenzene; 1-amino-2-[(2'-hydroxyethyl)-amino]-5-nitrobenzene; 1-(2'-hydroxyethoxy)-2-[(2'-hydroxyethyl)amino]-5-nitrobenzene; 1-[(2'-hydroxyethyl)amino]-2-nitrobenzene; 2-(di(2'-hydroxyethyl)amino]-5-nitrophenol; 2-[(2'-hydroxyethyl)amino]-1-methoxy-5-nitrobenzene; 2-amino-3-nitrophenol; 1-amino-2-methyl-6-nitrobenzene; 1-(2'-hydroxyethoxy)-3-methylamino-4-nitrobenzene; 2,3-(dihydroxypropoxy)-3-methylamino-4-nitrobenzene; 2-[(2'-hydroxyethyl)amino]-5-nitrophenol; 3-[(2'-aminoethyl)amino]-1-methoxy-4-nitrobenzene hydrochloride; 1-[(2'-ureidoethyl)amino]-4-nitrobenzene; 4-[(2',3'-dihydroxypropyl)-amino]-3-nitro-1-trifluoromethylbenzene; 1-chloro-2,4-bis-[(2'-hydroxyethyl)amino]-5-nitrobenzene; 1-amino-4-[(2'-aminoethyl)amino]-5-methyl-2-nitrobenzene; 4-[(2'-hydroxyethyl)amino]-3-nitro-1-methylbenzene; 1-chloro-4-[(2'-hydroxyethyl)amino]-3-nitrobenzene; 4-[(2'-hydroxyethyl)amino]-3-nitro-1-trifluoromethylbenzene; 4-[(2'-hydroxyethyl)amino]-3-nitrobenzonitrile; 4-[(2'-hydroxyethyl)amino]-3-nitrobenzamide; 3-[(2'-hydroxyethyl)amino]-4-methyl-1-nitrobenzene and 4-chloro-3-[(2'-hydroxyethyl)amino]-1-nitrobenzene.

Particularly preferred amines, aminonitrobenzenes or phenols are ethanolamine, 1,4-diaminobenzene; 1,4-diamino-2-methylbenzene; 1,4-diamino-2-(2'-hydroxyethyl)-benzene; 1,4-diamino-2-(1'-hydroxyethyl)benzene; 2,4-diamino-1-(2'-hydroxyethoxy)benzene; 2,4,5,6-tetraaminopyrimidine; hydroquinone; 5,6-diamino-2,4-dihydroxy-pyrimidine; 2,7-diaminofluorene; 1-amino-2-naphthol; 2,3-dihydro-3-methyl-2-benzothiazolone hydrazone; 2-aminophenol; 4,5-diamino-1-(2'-hydroxyethyl)-1H-pyrazole; 4,5-diamino-1-benzyl-1H-pyrazole; phenol; 4,5-diamino-1-[(4'-methylbenzyl)-1H-pyrazole; 4,5-diamino-1H-pyrazole; 4,5-diamino-1-methyl-1H-pyrazole; 4,5-diamino-(1-isopropyl)-1H-pyrazole; N-(3-dimethylaminophenyl)urea; 2-amino-4-[(2'-hydroxyethyl)amino]anisole; 1,3-diaminobenzene; 1,3-di[(2,4-diaminophenoxy)propane; 4-methylphenol; 4-aminophenol; 4-amino-3-methylphenol; 5-amino-2-methylphenol; 3-aminophenol; 1,3-dihydroxybenzene; 5-hydroxyindole; 4-[(2'-hydroxyethyl)amino]-3-nitro-1-methylbenzene; 4-[(2'-hydroxyethyl)amino]-3-nitrophenol; 2-amino-6-chloro-4-nitrophenol; 2-chloro-6-ethylamino-4-nitrophenol; 1-amino-2-[(2'-hydroxyethyl)-amino]-5-nitrobenzene as well as the 2,5-diaminonitrobenzenes, for example 1-(2'-hydroxyethyl)amino-2-nitro-4-[(di(2'-hydroxyethyl)amino]benzene, 1-amino-4-[di(2'-hydroxyethyl)amino]-2-nitrobenzene; 4-[di(2'-hydroxyethyl)amino]-1-[(2'-methoxyethyl)amino]-2-nitrobenzene; 4-[ethyl-(2'-hydroxyethyl)amino]-1-[(2'-hydroxy-ethyl)amino]-2-nitrobenzene; 1-amino-5-chloro-4-[(2',3'-dihydroxypropyl)amino]-2-nitrobenzene and 2,5-diamino-6-nitropyridine.

The compounds of formula (I) and the amines, aminonitrobenzenes or phenols are kept separate from each other and are mixed with each other shortly before use. If the compounds of formula (I) and the amines, aminonitrobenzenes and/or phenols are solids, however, it is also possible to package them together and to prepare the ready-for-use colorant (A) shortly before use by mixing the compounds of formula (I) and the amines, aminonitrobenzenes and/or phenols with water or with a liquid preparation containing the remaining constituents of the coloring agent.

Moreover, In addition to the compounds of formula (I) and to the amines, aminonitrobenzenes and phenols, the colorant of the invention can optionally contain in component (A2) and in the ready-for-use preparation (A) other common, physiologically innocuous, direct dyes from the group consisting of cationic and anionic dyes, disperse dyes, azo dyes, quinone dyes and triphenylmethane dyes.

These direct dyes can be used in component (A2) in a total amount from about 0.02 to about 20 wt. % and preferably from 0.2 to 10 wt. %, the total amount of direct dyes in the ready-for-use colorant (A) obtained by mixing components (A1) and (A2) being about 0.01 to about 10 wt. % and preferably 0.1 to 5 wt. %.

As a rule, the coloring agent of the invention consists of a mixture of components (A1) and (A2), namely of a dye carrier composition (A1) which contains the compound of formula (I), and an additional dye carrier composition (A2) which contains the amines, aminonitrobenzenes and/or phenols.

The compounds of formula (I) and the amines, aminonitrobenzenes and/or phenols are contained in their respective dye carrier composition [component (A1) or component (A2)] in a total amount from about 0.02 to about 20 wt. % and preferably from about 0.2 to about 10 wt. %, the compounds of formula (I) and the amines, aminonitrobenzenes and/or phenols being contained in the ready-for-use coloring agent (A) in a total amount from about 0.01 to about 10 wt. % and preferably from about 0.1 to about 5 wt. %.

Components (A1) and (A2) and the ready-for-use coloring agent (A) can be prepared in the form of a solution, particularly an aqueous or aqueous-alcoholic solution, or as a cream, a gel or an emulsion. Such a preparation consists of a mixture of the compound of formula (I) and of the amines, aminonitrobenzenes and/or phenols with the additives commonly used in such preparations.

Common additives for colorants used in the form of solutions, creams, emulsions, gels or aerosol foams are, for example, solvents such as water, the lower aliphatic alcohols, for example ethanol, n-propanol and isopropanol, or the polyols such as glycerol and 1,2-propandiol, moreover wetting agents or emulsifiers from the classes of anionic, cationic, amphoteric or nonionic surface-active substances such as the fatty alcohol sulfates, ethoxylated fatty alcohol sulfates, alkylsulfonates, alkylbenzenesulfonates, alkyltrimethylammonium salts, alkylbetaines, ethoxylated fatty alcohols*[1], ethoxylated nonylphenols*, fatty alkanolamides*, ethoxylated fatty esters, moreover thickeners such as the higher fatty alcohols, starch or cellulose derivatives, perfumes, hair-pretreatment agents, conditioners, hair swelling agents, preservatives, furthermore vaselines, paraffin oils and fatty acids as well as hair-care agents such as cationic resins, lanolin derivatives, cholesterol, pantothenic acid and betaine. The said constituents are used in amounts commonly employed for such purposes, for example the wetting agents and emulsifiers at a concentration of about 0.5 to about 30 wt. % [always based on component (A1) or (A2)], the thickeners in an amount from about 0.1 to about 25 wt. % [always based on component (A1) or component (A2)], and the hair-care agents at a concentration of about 0.1 to about 5.0 wt. % [always based on component (A1) or component (A2)].

[1] In the original German text, the compounds marked with an asterisk appear twice, obviously by mistake—Translator The pH of the ready-for-use colorant (A) is about 3 to about 12 and preferably about 4 to about 10 and as a rule is reached upon mixing component (A1) with component (A2). To adjust the pH of components (A1) and (A2) and of the ready-for-use colorant (A) to the value desired for the dyeing, an alkalinizing agent can be used if needed, for example an alkali metal hydroxide, alkaline earth metal hydroxide, alkali metal acetate, alkaline earth metal acetate, alkali metal carbonate or alkaline earth metal carbonate, or an acid, for example lactic acid, acetic acid, tartaric acid, phosphoric acid, hydrochloric acid, citric acid, ascorbic acid or boric acid.

The ready-for-use colorant is prepared just before use by mixing components (A1) and (A2), optionally by adding a base, for example sodium acetate, sodium bicarbonate or sodium carbonate, and is then applied to the fibers, particularly human hair. Depending on the depth of shade desired, this mixture is allowed to act for about 5 to about 60 minutes and preferably from about 15 to about 30 minutes at a temperature of about 20 to about 50° C. and particularly from about 30 to about 40° C. The fibers are then rinsed with water, optionally washed with a shampoo and then dried.

Another object of the present invention is a multicomponent kit consisting of a preparation of component (A1), a preparation of component (A2) and optionally an agent for adjusting the pH. The preparations of components (A1) and (A2) can, of course, also consists of several individual components which are mixed just before use. A 2-component kit is also possible, in which case the first component consists of a powder of a compound of formula (I), the amine, aminonitrobenzene and/or phenol and optionally other common powdered cosmetic additives, and the second component is water or a liquid cosmetic preparation. Particularly preferred, however, is a 2-component kit consisting of a preparation of component (A1) and a preparation of component (A2).

The coloring agent of the invention imparts to the fibers, particularly keratin fibers such as human hair, in a gentle manner, a uniform and long-lasting coloration, a wide range of yellow to dark-violet or brown-black color shades being possible.

Because of their high resistance to oxidants, the compounds of general formula (I) can also be used in oxidative colorants based on oxidation dye precursors. It is also possible to use the compounds of general formula (I) in brightening toners in which—for the purpose of brightening the hair to be dyed or of improving its luster—the direct dyes are used in combination with an oxidant.

The following examples illustrate the object of the invention without limiting its scope.

EXAMPLES

Examples 1 to 21

Hair Colorants

Component (A1)

| | |
|---|---|
| 0.5 g | of 7-chloro-4-nitro-2,1,3-benzoxadiazole |
| 5.0 g | of ethanol |
| 4.0 g | of decyl polyglucoside (aqueous solution; Plantaren ® 2000, supplied by Cognis, Germany) |
| 0.2 g | of disodium ethylenediaminetetraacetate hydrate |
| to 100.0 g | water, demineralized |

Component (A2)

| | |
|---|---|
| X g | of powdered amine and/or phenol as per Table 1. |

The aforesaid mixture [component (A1)] was mixed uniformly with the powder containing the amine or the phenol [component (A2)] at room temperature (20–25° C.) or with slight heating (35–40° C.)—optionally by adding a spatula tip-full of sodium acetate. If necessary, the pH was adjusted to the desired value with sodium hydroxide or citric acid.

The ready-for-use hair colorant thus obtained was applied to the hair and uniformly distributed with a brush. After an exposure time of 30 min at 40° C., the hair was rinsed with lukewarm water and then dried.

The amount of amine or phenol used and the resulting colorations are summarized in the following Table 1.

TABLE 1

| Example No. | Amine or Phenol Used (amount in g) | pH | Shade After Dyeing | Color values L | a | b |
|---|---|---|---|---|---|---|
| 1 | ethanolamine (0.153 g) | 9.3 | yellow | +41.16 | +11.42 | +43.41 |
| 2 | phenol (0.235 g) | 3.5 | yellow | +57.82 | +8.43 | +62.90 |
| 3 | hydroquinone (0.275 g) | 7.0 | orange | +69.52 | +2.72 | +46.43 |
| 4 | 4-dimethylamino-aniline (0.340 g) | 4.6 | violet | +31.83 | +13.15 | −2.80 |

TABLE 1-continued

| Example No. | Amine or Phenol Used (amount in g) | pH | Shade After Dyeing | Color values L | a | b |
|---|---|---|---|---|---|---|
| 5 | 1,4-diaminobenzene (0.270 g) | 4.7 | violet | +26.36 | +23.37 | −0.48 |
| 6 | 1,4-diamino-2-methylbenzene.HCl (0.055 g) | 4.5 | violet | +30.81 | +21.60 | +0.28 |
| 7 | 1,4-diamino-2-(2-hydroxyethyl)-benzene sulfate (0.630 g) | 3.9 | violet | +21.33 | +17.74 | +2.16 |
| 8 | 4-aminophenol (0.273 g) | 3.4 | ruby-red | +26.13 | +39.62 | +15.48 |
| 9 | 2,4,5,6-tetraamino-pyrimidine sulfate (0.640 g) | 9.8 | green-brown | +34.85 | +4.30 | +18.31 |
| 10 | 5,6-diamino-2,4-dihydroxypyrimidine sulfate (0.455 g) | 7.3 | brown-orange | +32.73 | +15.18 | +28.79 |
| 11 | 4,5-diamino-1-(2'-hydroxyethyl)-1H-pyrazole sulfate (0.600 g) | 9.3 | red | +29.07 | +38.14 | +22.13 |
| 12 | 2,7-diaminofluorene (0.490 g) | 7.4 | violet | +26.95 | +18.76 | +5.13 |
| 13 | 1-amino-2-naphthol.HCl (0.489 g) | 6.3 | brown | +41.52 | +7.03 | +20.43 |
| 14 | 2,3-dihydro-3-methyl-2-benzothiazolone hydrazone.HCl (0.584 g) | 6.4 | orange | +44.00 | +40.62 | +46.52 |
| 15 | N-(3-dimethylamino-phenyl)urea (0.448 g) | 6.5 | yellow-brown | +35.42 | +1.75 | +14.81 |
| 16 | 2-amino-4-[(2'-hydroxyethyl)amino]-anisole sulfate (0.746 g) | 6.7 | gray | +47.79 | −2.78 | +1.60 |
| 17 | 1,3-diaminobenzene (0.270 g) | 4.3 | red-violet | +32.31 | +18.33 | +11.25 |
| 18 | 2,4-diamino-1-(2'-hydroxyethoxy)benzene sulfate (0.666 g) | 4.1 | blue-violet | +26.41 | +4.77 | −2.69 |
| 19 | 5-amino-2-methyl-phenol (0.308 g) | 4.5 | ruby-red | +32.96 | +39.20 | +24.27 |
| 20 | 3-aminophenol (0.273 g) | 4.4 | ruby-red | +38.98 | +40.37 | +34.32 |
| 21 | 1,3-dihydroxy-benzene (0.275 g) | 4.0 | yellow | +70.64 | +8.37 | +47.07 |

Examples 22 to 28

Hair Colorants

Component (A1):

| 1.0 g | of 7-chloro-4-nitro-2,1,3-benzoxadiazole |
|---|---|
| 5.0 g | of ethanol |
| 4.0 g | of decyl polyglucoside (Plantaren ® 2000), aqueous solution |
| 0.2 g | of disodium ethylenediaminetetraacetate hydrate |
| to 100.0 g | water, demineralized |

Component (A2):

| X g | of amine or phenol as per Table 2 |
|---|---|
| 5.0 g | of ethanol |
| 4.0 g | of decyl polyglucoside (Plantaren ® 2000), aqueous solution |
| 0.2 g | of disodium ethylenediaminetetraacetate hydrate |
| to 100.0 g | water, demineralized |

10 g of component (A1) was mixed uniformly with 10 g of component (A2) at room temperature (20–25° C.) or with slight heating (35–40° C.)—optionally by adding a spatula tip-full of sodium acetate. If necessary, the pH was adjusted to the desired value with sodium hydroxide or citric acid.

The ready-for-use hair colorant thus obtained was applied to the hair and uniformly distributed with a brush. After an exposure time of 30 min at 40° C., the hair was rinsed with lukewarm water and then dried.

The amount of amine or phenol used and the resulting colorations are summarized in the following Table 2.

TABLE 2

| Example No. | Amine or Phenol Used (amount in g) | pH | Shade After Dyeing | Color values L | a | b |
|---|---|---|---|---|---|---|
| 22 | 1,4-diaminobenzene (0.540 g) | 4.8<br>6.8<br>9.8 | violet | +21.77<br>+26.66<br>+30.48 | +20.65<br>+25.47<br>+24.70 | +0.80<br>−1.39<br>−0.35 |
| 23 | 1,4-diamino-2-methylbenzene sulfate (1.100 g) | 4.7<br>6.8<br>10.0 | violet | +21.69<br>+29.24<br>+30.14 | +19.99<br>+22.23<br>+19.04 | +3.57<br>+5.84<br>+4.62 |
| 24 | 4-aminophenol (0.546 g) | 4.6<br>6.9<br>9.5 | ruby-red | +23.87<br>+25.30<br>+23.31 | +35.97<br>+39.15<br>+35.70 | +13.01<br>+14.64<br>+12.80 |
| 25 | 2-aminophenol (0.546 g) | 4.8<br>6.6<br>9.2 | red-orange | +34.39<br>+34.59<br>+32.15 | +40.22<br>+39.94<br>+34.18 | +29.97<br>+30.89<br>+38.30 |
| 26 | phenol (0.470 g) | 4.7<br>6.8<br>9.8 | yellow | +67.34<br>+62.29<br>+68.61 | +6.41<br>+9.85<br>+4.33 | +76.05<br>+73.75<br>+70.47 |
| 27 | phenol (0.234 g) and 1,4-diamino-2-methylbenzene sulfate (0.550 g) | 4.3<br>7.7<br>10.0 | pink-violet | +43.82<br>+47.73<br>+37.17 | +22.25<br>+20.71<br>+20.80 | +12.60<br>+8.74<br>+2.67 |
| 28 | 2-aminophenol (0.272 g) and 4-aminophenol (0.272 g) | 4.4<br>7.7<br>9.5 | ruby-red | +23.96<br>+21.82<br>+21.95 | +35.28<br>+30.59<br>+27.56 | +13.08<br>+10.46<br>+10.03 |

Examples 29 and 30

Hair Colorants in Cream Form

Component (A1):

| | |
|---|---|
| 1 g | of 7-chloro-4-nitro-2,1,3-benzoxadiazole |
| 12 g | of cetearyl alcohol |
| 10 g | of lauryl ether sulfate, 28% aqueous solution |
| 20 g | of ethanol |
| to 100 g | water, demineralized |

The cetearyl alcohol was melted at 80° C. The lauryl ether sulfate was heated to 80° C. with 95% of the water and added to the molten cetearyl alcohol. The mixture was stirred until a cream formed. The 7-chloro-4-nitro-2,1,3-benzoxadiazole was mixed with the ethanol and the remainder of the water at room temperature and the resulting mixture was added to the cream. The pH of the cream thus obtained was 4.6.

Component (A2)

| | |
|---|---|
| X g | of the amine or phenol as per Table 3 |
| 12 g | of cetearyl alcohol |
| 10 g | of lauryl ether sulfate, 28% aqueous solution |
| 20 g | of ethanol |
| to 100 g | water, demineralized |

The cetearyl alcohol was melted at 80° C. The lauryl ether sulfate was heated to 80° C. with 95% of the water and added to the molten cetearyl alcohol. The mixture was stirred until a cream formed. The amine or the phenol was mixed with the ethanol and the remainder of the water at room temperature, and the resulting mixture was added to the cream. The pH of the cream thus obtained was adjusted to 7 (optionally with addition of sodium acetate).

Components (A1) and (A2) were mixed with one another in a 1:1 ratio. Optionally a spatula tip-full of sodium acetate was added. If needed, the pH of the ready-for-use colorant was adjusted to the desired value with sodium hydroxide or citric acid. The resulting ready-for-use hair colorant was applied to the hair and uniformly distributed with a brush. After an exposure time of 30 min at 40° C., the hair was washed with a shampoo, rinsed with lukewarm water and then dried.

The amount of amine or phenol used and the resulting colorations are summarized in the following Table 3.

TABLE 3

| Example No. | Amine or Phenol Used (amount in g) | pH | Shade After Dyeing | Color values L | a | b |
|---|---|---|---|---|---|---|
| 29 | 1,4-diaminobenzene (1.350 g) | 7.2 | violet | +20.8 | +20.3 | +1.4 |
| 30 | 4-aminophenol (1.370 g) | 7.3 | ruby-red | +22.4 | +35.7 | +11.4 |

Examples 31 to 42

Hair Colorants

Component (A1)

| | |
|---|---|
| 1.0 g | of 7-chloro-4-nitro-2,1,3-benzoxadiazole |
| 5.0 g | of ethanol |
| 4.0 g | of decyl polyglucoside (aqueous solution; Plantaren ® 2000, supplied by Cognis, Germany) |
| 0.2 g | of disodium ethylenediaminetetraacetate hydrate |
| to 100.0 g | water, demineralized |

-continued

Component (A2)

| | |
|---|---|
| X g | of aminonitrobenzene as per Table 4 |
| 5.0 g | of ethanol |
| 4.0 g | of decyl polyglucoside (Plantaren ® 2000), aqueous solution |
| 0.2 g | of disodium ethylenediaminetetraacetate hydrate |
| to 100.0 g | water, demineralized |

10 g of component (A1) was mixed uniformly with 10 g of component (A2) at room temperature (20–25° C.) or with slight heating (35–40° C.)—optionally by adding a spatula tip-full of sodium acetate. If necessary, the mixture was heated at 40 to 60° C. for 15 minutes. When needed, the pH was adjusted to the desired value with sodium hydroxide or citric acid.

The ready-for-use hair colorant thus obtained was applied to the hair and uniformly distributed with a brush. After an exposure time of 30 min at 40° C., the hair was rinsed with lukewarm water and then dried.

The amount of aminonitrobenzene used and the resulting colorations are summarized in the following Table 4.

TABLE 4

| Example No. | Aminonitrobenzene Used (amount in g) | pH | Shade After Dyeing | Color values | | |
|---|---|---|---|---|---|---|
| | | | | L | a | b |
| 31 | 1-(2'-hydroxyethyl)-amino-2-nitro-4-[(di-(2'-hydroxyethyl)-amino]benzene (1.420 g) | 6.3 | brown-black with violet reflexes | +17.19 | +3.94 | +2.43 |
| 32 | 4-di[(2'-hydroxy-ethyl)amino]-1-[(2-methoxyethyl)-amino]-2-nitro-benzene (1.490 g) | 4.9 | brown-black with violet reflexes | +18.47 | +5.56 | +3.59 |
| 33 | 4-[ethyl-(2'-hydroxy-ethyl)amino]-1-[(2'-hydroxyethyl)amino]-2-nitrobenzene.HCl (1.520 g) | 5.4 | brown-black with violet reflexes | +18.27 | +3.45 | +2.71 |
| 34 | 1-amino-4-[di(2'-hydroxyethyl)amino]-2-nitrobenzene.HCl (1.200 g) | 5.2 | brown with red reflexes | +18.10 | +10.07 | +3.93 |
| 35 | 1-amino-5-chloro-4-[(2',3'-dihydroxy-propyl)amino]-2-nitrobenzene (1.300 g) | 7.0 | cherry-red | +20.35 | +24.84 | +7.43 |
| 36 | 1-amino-2-[(2'-hydroxyethyl)amino]-5-nitrobenzene (0.980 g) | 10.0 | red-orange | +29.98 | +34.15 | +23.20 |
| 37 | 4-[(2'-hydroxyethyl)-amino]-3-nitro-1-methylbenzene (0.980 g) | 0.4 | orange | +51.18 | +30.12 | +59.68 |
| 38 | 4-[(2'-hydroxyethyl)-amino]-3-nitro-phenol (0.990 g) | 6.2 | ruby-red | +30.91 | +48.81 | +25.69 |
| 39 | 2-amino-6-chloro-4-nitrophenol.HCl (1.120 g) | 4.7 | brown-violet | +17.74 | +15.06 | +4.19 |
| 40 | 2-chloro-6-ethyl-amino-4-nitro-phenol (1.080 g) | 7.5 | red | +29.73 | +38.89 | +23.40 |
| 41 | 2,5-diamino-6-nitro-pyridine (0.770 g) | 6.5 | orange | +39.10 | +37.92 | +40.11 |
| 42 | 1-amino-4-[di(2'-hydroxyethyl)amino]-2-nitrobenzene.HCl (0.60 g) and 4-[di-(2'-hydroxyethyl)-amino]-1-[(2'-methoxyethyl)-amino]-2-nitro-benzene (0.750 g) | 4.8 | brown with red reflexes | +18.76 | +9.46 | +3.08 |

Examples 43 to 51

Hair Colorants

Component (A1)

| | |
|---|---|
| 0.488 g | of 7-methoxy-4-nitro-2,1,3-benzoxadiazole |
| 5.0 g | of ethanol |
| 4.0 g | of decyl polyglucoside (aqueous solution; Plantaren ® 2000, supplied by Cognis, Germany) |
| 0.2 g | of disodium ethylenediaminetetraacetate hydrate |
| to 100.0 g | water, demineralized |

Component (A2)

| | |
|---|---|
| X g | of powdered amine and/or phenol as per Table 5. |

The aforesaid mixture [component (A1)] was mixed uniformly with the powder containing the amine or the phenol [component (A2)] at room temperature (20–25° C.) or with slight heating (35–40° C.)—optionally by adding a spatula tip-full of sodium acetate. If necessary, the pH was adjusted to the desired value with sodium hydroxide or citric acid.

The ready-for-use hair colorant thus obtained was applied to the hair and uniformly distributed with a brush. After an exposure time of 30 min at 40° C., the hair was rinsed with lukewarm water and then dried.

The amount of amine or phenol used and the resulting colorations are summarized in the following Table 5.

Unless otherwise indicated, all percentages in the present patent application are by weight.

What is claimed is:

1. Fiber-coloring agent (A) prepared by mixing two components (A1) and (A2), characterized in that component (A1) contains at least one compound of formula (I)

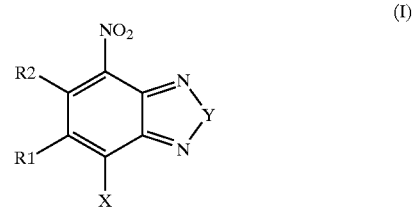

wherein X denotes a halogen atom, a methoxy group or an ethoxy group; Y denotes an oxygen atom, a sulfur atom or a selenium atom; R1 and R2 are equal or different and independently of each other denote hydrogen, a halogen atom, a $(C_1-C_4)$-alkyl group, a halogen-substituted $(C_1-C_4)$-alkyl group, a $(C_1-C_4)$-alkoxy group, a nitro group, an acetamido group or an $NR^aR^b$ group, wherein the $R^a$ and $R^b$ groups are equal or different and independently of each other denote hydrogen, a $(C_1-C_4)$-alkyl group, an optionally substituted aromatic carbon ring or a $(C_1-C_4)$-alkanecarbonyl group, or $R^a$ and $R^b$ together with the nitrogen atom form a heterocyclic $(C_3-C_6)$ group; and component (A2) contains at least one compound selected from the group consisting of amines, aminobenzenes and phenols.

TABLE 5

| Example No. | Amine or Phenol Used (amount in g) | pH | Shade After Dyeing | Color values | | |
|---|---|---|---|---|---|---|
| | | | | L | a | b |
| 43 | 1,4-diamino-2-methylbenzene sulfate (0.55 g) | 4.7 | violet | +21.82 | +19.70 | +2.28 |
| 44 | 1,4-diamino-2-(2-hydroxyethyl)benzene sulfate (0.63 g) | 4.6 | violet | +17.75 | +11.85 | +1.25 |
| 45 | 4-aminophenol (0.273 g) | 7.6 | ruby-red | +31.05 | +46.43 | +20.06 |
| 46 | 4-amino-3-methylphenol [no amount given-Translator] | 9.3 | orange | +44.84 | +32.42 | +43.04 |
| 47 | 4,5-diamino-1-(2'-hydroxyethyl)-1H-pyrazole sulfate (0.600 g) | 9.9 | red | +28.26 | +34.16 | +17.99 |
| 48 | 2,4-diamino-1-(2'-hydroxyethoxy)-benzene sulfate (0.660 g) | 4.4 | red-violet | +28.41 | +31.66 | +11.88 |
| 49 | 5-amino-2-methylphenol (0.308 g) | 4.7 | red | +46.23 | +48.47 | +28.73 |
| 50 | 3-aminophenol (0.273 g) | 4.2 | red-orange | +44.08 | +51.80 | +44.28 |
| 51 | 1,3-dihydroxybenzene (0.275 g) | 4.8 | yellow | +78.59 | −0.89 | +62.74 |

The L*a*b* values given in the preceding examples were determined with a Chromameter II color meter supplied by Minolta. The L value indicates the brightness (namely the lower the L value the higher is the color intensity), whereas the a-value is a measure of the red content (namely the higher the a-value the higher is the red content). The b-value is a measure of the blue content of the color, the blue content being the higher the more negative is the b-value.

2. Agent according to claim 1, characterized in that the compound of formula (I) is selected from, the group consisting of 4-nitro-2,1,3-benzoxadiazoles, 4-nitro-2,1,3-benzothiadiazoles 4-nitro-2,1,3-benzoselenadiazoles with 4-chloro-7-nitro-2,1,3-benzoxadiazole; 4-bromo-7-nitro-2,1,3-benzoxadiazole; 4-fluoro-7-nitro-2,1,3-benzoxadiazole, 4-methoxy-7-nitro-2,1,3-benzoxadiazole, 4-ethoxy-7-nitro-2,1,3-benzoxadiazole, 4-chloro-5,7-dinitro-2,1,3- benzoxadiazole, 5,7-dichloro-4-nitro-2,1,3-benzoxadiazole, 5,7-dibromo-4-nitro-2,1,3-benzoxadiazole, 7-chloro-4-nitro-5-diethylamino-2,1,3-benzoxadiazole, 5-amino-7-chloro-4-nitro-2,1,3-benzoxadiazole, 7-chloro-4-nitro-5-(1-piperidinyl)-2,1,3-benzoxadiazole, 4-chloro-7-nitro-2,1,3-benzothiadiazole, 4-bromo-7-nitro-2,1,3-benzothiadiazole, 4-methoxy-7-nitro-2,1,3-benzothiadiazole, 4-ethoxy-7-nitro-2,1,3-benzothiadiazole, 4-chloro-5,7-dinitro-2,1,3-benzothiadiazole, 4-bromo-5,7-dinitro-2,1,3-benzothiadiazole, 4,5-dichloro-7-nitro-2,1,3-benzothiadiazole, 5,7-dichloro-4-nitro-2,1,3-benzothiadiazole, 4,5-dibromo-7-nitro-2,1,3-benzothiadiazole, 5,7-dibromo-4-nitro-2,1,3-benzothiadiazole, 4,6-dichloro-5,7-dinitro-2,1,3-benzothiadiazole, 4,6-dibromo-5,7-dinitro-2,1,3-benzothiadiazole, 5-chloro-7-fluoro-4-nitro-2,1,3-benzothiadiazole, 5-anilino-7-bromo-4-nitro-2,1,3-benzothiadiazole, 5-amino-7-chloro-4-nitro-2,1,3-benzothiadiazole,7-bromo-5-(diethylamino)-4-nitro-2,1,3-benzothiadiazole,4-chloro-5-methyl-7-nitro-2,1,3-benzothiadiazole, 4-bromo-5-methyl-4-nitro-2,1,3-benzothiadiazole, 7-bromo-5-(bromomethyl)-7-nitro-2,1,3-benzothiadiazole, N-(7-chloro-4-nitro-2,1,3-benzothiadiazole-5-yl)acetamide, 4-chloro-7-nitro-2,1,3-benzoselenadiazole; 4-bromo-7-nitro-2,1,3-benzoselenadiazole, 4-methoxy-7-nitro-2,1,3-benzoselenadiazole, 4-ethoxy-7-nitro-2,1,3-benzoselenadiazole, 5,7-dibromo-4-nitro-2,1,3-benzoselenadiazole, 5,7-dichloro-4-nitro-2,1,3-benzoselenadiazole, 7-bromo-5-methyl-4-nitro-2,1,3-benzoselenadiazole and 7-bromo-5-(bromomethyl)-4-nitro-2,1,3-benzoselenadiazole.

3. Agent according to claim 1, characterized in that the amine, aminonitrobenzene and phenol are selected from the group consisting of ethanolamine, 1,4-diaminobenzene, 1,4-diamino-2-methylbenzene, 1,4-diamino-2-(2'-hydroxyethyl)benzene, 1,4-diamino-2-(1'-hydroxyethyl)benzene, 2,4-diamino-1-(2'-hydroxyethoxy)benzene, 2,4,5,6-tetraaminopyrimidine, hydroquinone, 5,6-diamino-2,4-dihydroxypyrimidine; 2,7-diaminofluorene; 1-amino-2-naphthol, 2,3-dihydro-3-methyl-2-benzothiazolone hydrazone, 2-aminophenol, 4,5-diamino-1-(2'-hydroxyethyl)-1H-pyrazole, 4,5-diamino-1-benzyl-1H-pyrazole, phenol, 4,5-diamino-1-[(4'-methylbenzyl)-1H-pyrazole; 4,5-diamino-1-methyl-1H-pyrazole, 4,5-diamino-(1-isopropyl)-1H-pyrazole, N-(3-dimethylaminophenyl)urea, 2-amino-4-[(2'-hydroxyethyl)amino]anisole, 1,3-diaminobenzene, 1,3-di(2,4-diaminophenoxy)propane, 4-methylphenol, 4-aminophenol, 4-amino-3-methylphenol, 5-amino-2-methylphenol, 3-aminophenol, 1,3-dihydroxybenzene, 5-hydroxyindole, 4-[(2'-hydroxyethyl)amino]-3-nitro-1-methylbenzene, 4-[(2'-hydroxyethyl)amino]-3-nitrophenol, 2-amino-6-chloro-4-nitrophenol, 2-chloro-6-ethylamino-4-nitrophenol, 1-amino-2-[(2'-hydroxyethyl)amino]-5-nitrobenzene as well as the 2,5-diaminonitrobenzenes, for example 1-(2'-hydroxyethyl)amino-2-nitro-4-[(di-(2'-hydroxyethyl)amino]benzene, 1-amino-4-[di(2'-hydroxyethyl)amino]-2-nitrobenzene, 4-[di(2'-hydroxyethyl)amino]-1-[(2'-methoxyethyl)amino]-2-nitrobenzene, 4-[ethyl-(2'-hydroxyethyl)amino]-1-[(2'-hydroxyethyl)-amino]-2-nitrobenzene, 1-amino-5-chloro-4-[(2',3'-dihydroxypropyl)amino]-2-nitrobenzene and 2,5-diamino-6-nitropyridine.

4. Agent according to claim 1, characterized in that the compounds of formula (I) and the amines, aminonitrobenzenes and/or phenols are contained in the dye carrier [component (A1) or component (A2)] in a total amount from 0.02 to 20 wt. %.

5. Agent according to claim 1, characterized in that the compounds of formula (I) and the amines, aminonitrobenzenes and/or phenols are contained in the ready-for-use hair colorant (A) in a total amount from 0.01 to 10 wt. %.

6. Agent according to claim 1, characterized in that it contains additionally from 0.02 to 20 wt. % of a physiologically innocuous, direct dye selected from the group consisting of cationic and anionic dyes, disperse dyes, nitro dyes, azo dyes, quinone dyes and triphenylmethane dyes.

7. Agent according to claim 1, characterized in that the ready-for-use colorant (A) has a pH from 3 to 12.

8. Agent according to claim 1, characterized in that it additionally contains an oxidation dye precursor.

9. Agent according to claim 1, characterized in that it is mixed with an oxidant before use.

10. Agent according to claim 1, characterized in that it is a hair-coloring agent.

11. Hair-dyeing method whereby the ready-for-use coloring agent (A) is prepared immediately before use by mixing two components (A1) and (A2), optionally with addition of sodium acetate, and is then applied to the hair and allowed to act for 5 to 60 minutes at a temperature of 20 to 50° C., the hair then being rinsed with water, optionally washed with a shampoo, and then dried, characterized in that a coloring agent (A) obtained by mixing two components (A1) and (A2) according to claim 1 is used.

12. Multicomponent kit for dyeing hair, consisting of a preparation of component (A1) according to claim 1 and of a preparation of (A2) according to one of claim 1 and optionally of an agent for adjusting the pH.

13. Use of a combination of at least one compound of formula (I)

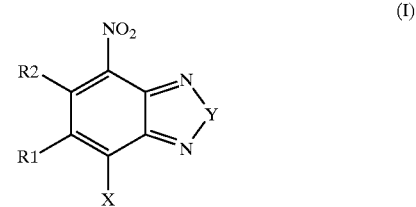

wherein X denotes a halogen atom, a methoxy group or an ethoxy group, Y denotes an oxygen atom, a sulfur atom or a selenium atom, R1 and R2 are equal or different and independently of each other denote hydrogen, a halogen atom, a $(C_1–C_4)$-alkyl group, a halogen-substituted $(C_1–C_4)$-alkyl group, a $(C_1–C_4)$-alkoxy group, a nitro group, an acetamido group or an $NR^aR^b$ group, wherein the $R^a$ and $R^b$ groups are equal or different and independently of each other denote hydrogen, a $(C_1–C_4)$-alkyl group, an optionally substituted aromatic carbon ring or a $(C_1–C_4)$-alkanecarbonyl group, or $R^a$ and $R^b$ together with the nitrogen atom form a heterocyclic $(C_3–C_6)$ group, and at least one compound selected from the group consisting of amines, aminonitrobenzenes and phenols, for dyeing keratin fibers.

* * * * *